United States Patent
Donella et al.

(10) Patent No.: US 10,583,569 B2
(45) Date of Patent: Mar. 10, 2020

(54) ARTICULATED DEVICE FOR ROBOTIC SYSTEMS

(71) Applicant: VALUEBIOTECH S.R.L., Milan (IT)

(72) Inventors: Nicolò Donella, Milan (IT); Alberto Giovanni Pansini, Catania (IT); Federica Iovine, Falciano di Caserta (IT); Louis Judah Jauvtis, Safnern (CH); Renzo Zaltieri, Agrate Brianza (IT); Antonello Forgione, Milan (IT); Filippo Righetto, Milan (IT)

(73) Assignee: VALUEBIOTECH S.R.L., Milan (IT)

( * ) Notice: Subject to any disclaimer, the term of this patent is extended or adjusted under 35 U.S.C. 154(b) by 379 days.

(21) Appl. No.: 15/502,140

(22) PCT Filed: Aug. 5, 2015

(86) PCT No.: PCT/EP2015/068102
§ 371 (c)(1),
(2) Date: Feb. 6, 2017

(87) PCT Pub. No.: WO2016/020456
PCT Pub. Date: Feb. 11, 2016

(65) Prior Publication Data
US 2017/0225340 A1 Aug. 10, 2017

(30) Foreign Application Priority Data
Aug. 8, 2014 (IT) ................ MI2014A1473

(51) Int. Cl.
*B25J 17/00* (2006.01)
*B25J 17/02* (2006.01)
(Continued)

(52) U.S. Cl.
CPC ............ *B25J 17/02* (2013.01); *A61B 34/30* (2016.02); *B25J 17/0291* (2013.01);
(Continued)

(58) Field of Classification Search
CPC ............................. B25J 17/02; B25J 17/0291
See application file for complete search history.

(56) References Cited

U.S. PATENT DOCUMENTS

| 4,246,661 A | 1/1981 | Pinson |
| 4,402,234 A * | 9/1983 | Malarz ................ B25J 19/0029 |
| | | 269/61 |

(Continued)

FOREIGN PATENT DOCUMENTS

| EP | 0080325 A1 | 6/1983 |
| EP | 0146682 A1 | 7/1985 |

(Continued)

OTHER PUBLICATIONS

International Search Report dated Nov. 2, 2015 re: Application No. PCT/EP2015/068102; pp. 1-4; citing: EP 0 080 325 A1, U.S. Pat. No. 5,887,800 A, EP 0 146 682 A1, EP 0 242 438 A1, US 2013/305869 A1, EP 2 514 574 A1 and U.S. Pat. No. 4,246,661 A.

(Continued)

*Primary Examiner* — Jake Cook
(74) *Attorney, Agent, or Firm* — Cantor Colburn LLP

(57) ABSTRACT

An articulated device for robotic systems includes three rigid bodies.
The first rigid body is configured to rotate about a first rotation axis with respect to a rigid base body.
The second rigid body is configured to rotate about a second rotation axis with respect to the first rigid body.
The third rigid body is configured to rotate about a third rotation axis with respect to the second rigid body.
The first, second, and third rotation axes coincide in at least one point which defines the center of rotation of the articulated device.

11 Claims, 19 Drawing Sheets

(51) Int. Cl.
  *B25J 18/00* (2006.01)
  *A61B 34/30* (2016.01)

(52) U.S. Cl.
  CPC ... *A61B 2034/302* (2016.02); *A61B 2034/305* (2016.02); *Y10S 901/26* (2013.01); *Y10S 901/29* (2013.01)

(56) References Cited

U.S. PATENT DOCUMENTS

| | | | |
|---|---|---|---|
| 4,662,815 A * | 5/1987 | Zimmer | B25J 17/0291 414/735 |
| 4,690,012 A * | 9/1987 | Dahlquist | B25J 17/0291 74/417 |
| 4,708,580 A * | 11/1987 | Akeel | B25J 19/0029 277/412 |
| 5,887,800 A | 3/1999 | McClosky | |
| 2013/0305869 A1 | 11/2013 | Krumbacher | |
| 2014/0116182 A1 * | 5/2014 | Long | B25J 9/102 74/490.04 |

FOREIGN PATENT DOCUMENTS

| | | |
|---|---|---|
| EP | 0242438 A1 | 10/1987 |
| EP | 2514574 A1 | 10/2012 |

OTHER PUBLICATIONS

Written Opinion dated Nov. 2, 2015 re: Application No. PCT/EP2015/068102; pp. 1-7; citing: EP 0 080 325 A1, U.S. Pat. No. 5,887,800 A, EP 0 146 682 A1, EP 0 242 438 A1, US 2013/305869 A1, and EP 2 514 574 A1.

* cited by examiner

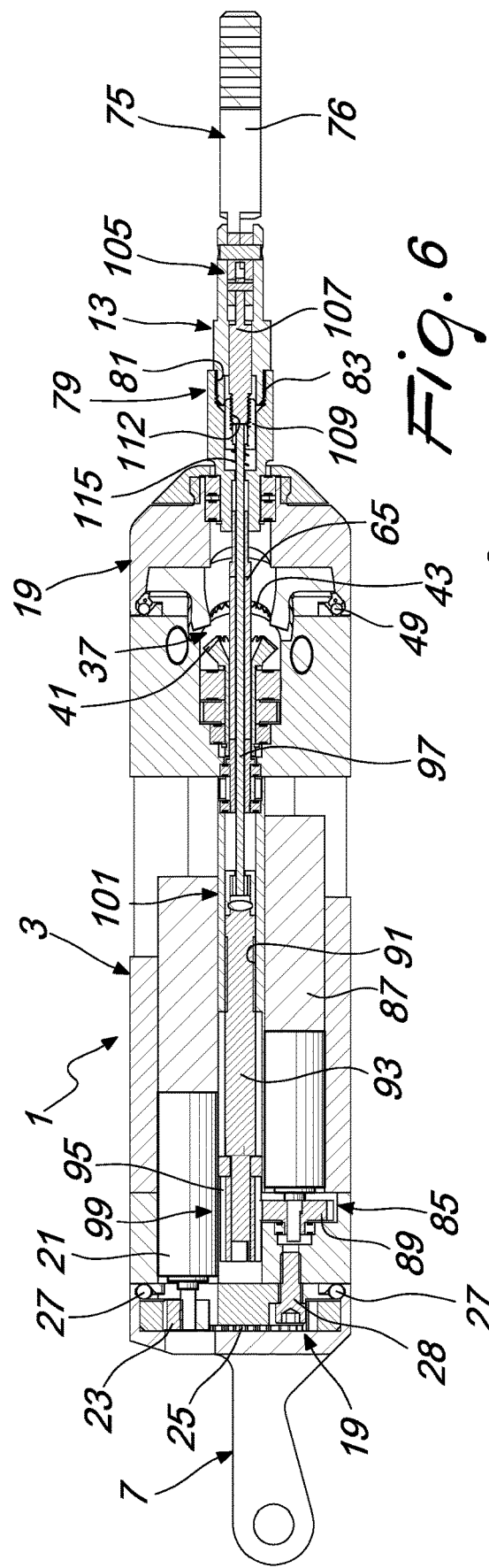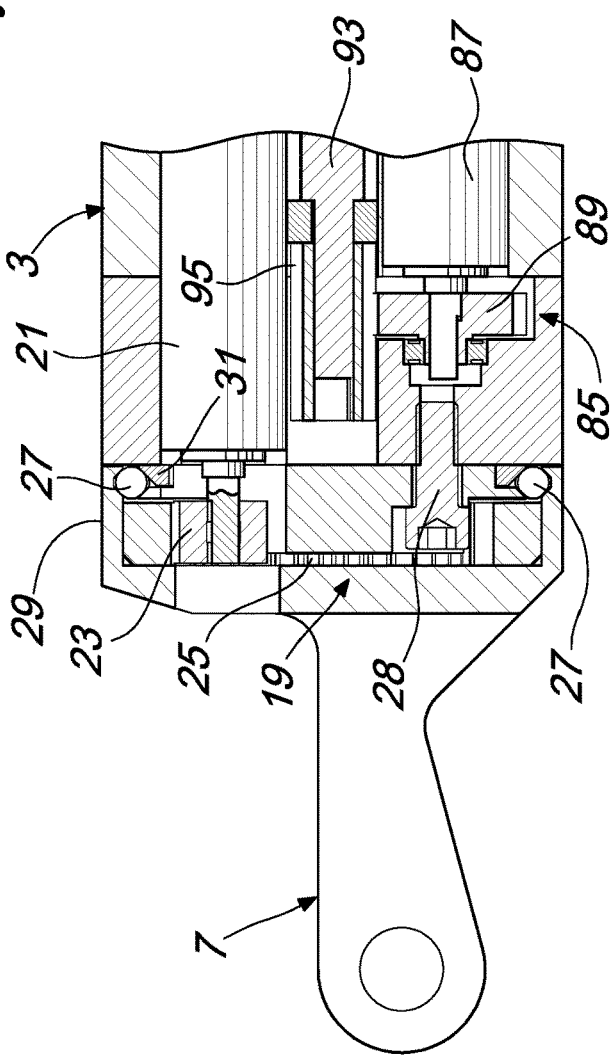

ARTICULATED DEVICE FOR ROBOTIC SYSTEMS

TECHNICAL FIELD

The present disclosure relates to an articulated device for robotic systems, which is particularly adapted for use in robotic systems requiring particular dexterity, such as, for example, robotic systems operating in the field of robotic surgery and in particular in the field of minimally-invasive robotic surgery.

BACKGROUND

Various types of articulated device for robotic systems are currently known and provide the desired degrees of freedom to the robotic system as a whole, as a function of the particular operations that the robotic system must perform.

Conventional articulated devices are not free from drawbacks, which include the fact that in order to provide the desired degrees of freedom to the robotic system, and therefore allow complex movements thereof, they are bulky and require large work spaces.

Another drawback of these conventional articulated devices is that they are difficult to miniaturize and they are therefore inadequate for application in the field of robotic surgery and particularly in the field of minimally-invasive robotic surgery.

SUMMARY

The aim of the present disclosure is to provide an articulated device that overcomes the limitations of the background art, making it possible to achieve considerable dexterity.

Within this aim, the present disclosure provides a miniaturized articulated device.

The disclosure also provides an articulated device that is particularly adapted for use in robotic systems for minimally-invasive robotic surgery.

The disclosure further provides an articulated device that is capable of giving the greatest assurances of reliability and safety in use.

The disclosure provides an articulated device that is easy to provide and economically and technically competitive when compared with the background art.

These aims and objectives and others that will become better apparent hereinafter are all achieved by providing an articulated device comprising:
- a first rigid body, which is configured to rotate about a first rotation axis with respect to a rigid base body,
- a second rigid body, which is configured to rotate about a second rotation axis with respect to said first rigid body, and
- a third rigid body, which is configured to rotate about a third rotation axis with respect to said second rigid body, wherein said first rotation axis, said second rotation axis and said third rotation axis coincide in at least one point, which defines the center of rotation of said articulated device.

BRIEF DESCRIPTION OF THE DRAWINGS

Further characteristics and advantages will become better apparent from the description of a preferred, but not exclusive, embodiment of an articulated device, which is illustrated by way of non-limiting example with the aid of the accompanying drawings, wherein:

FIG. 6 is a transverse cross-sectional view of the articulated device in FIG. 1, according to the disclosure;

FIG. 7 is an enlarged-scale view of a portion of FIG. 6;

In particular, FIG. 18 is a side view of a part of the articulated device, according to the disclosure, in a first operating configuration;

FIG. 19 is a cross-sectional side view of FIG. 18;

FIG. 20 is a side view of the same part of the articulated device, according to the disclosure, illustrated in FIG. 18, in a second operating configuration;

FIG. 21 is a cross-sectional side view of FIG. 20;

FIG. 22 is a view of two mechanical motion transmission components, according to the alternative embodiment of the rotation means shown in the preceding FIGS. 18 to 21.

DETAILED DESCRIPTION OF THE DRAWINGS

Figure 1:
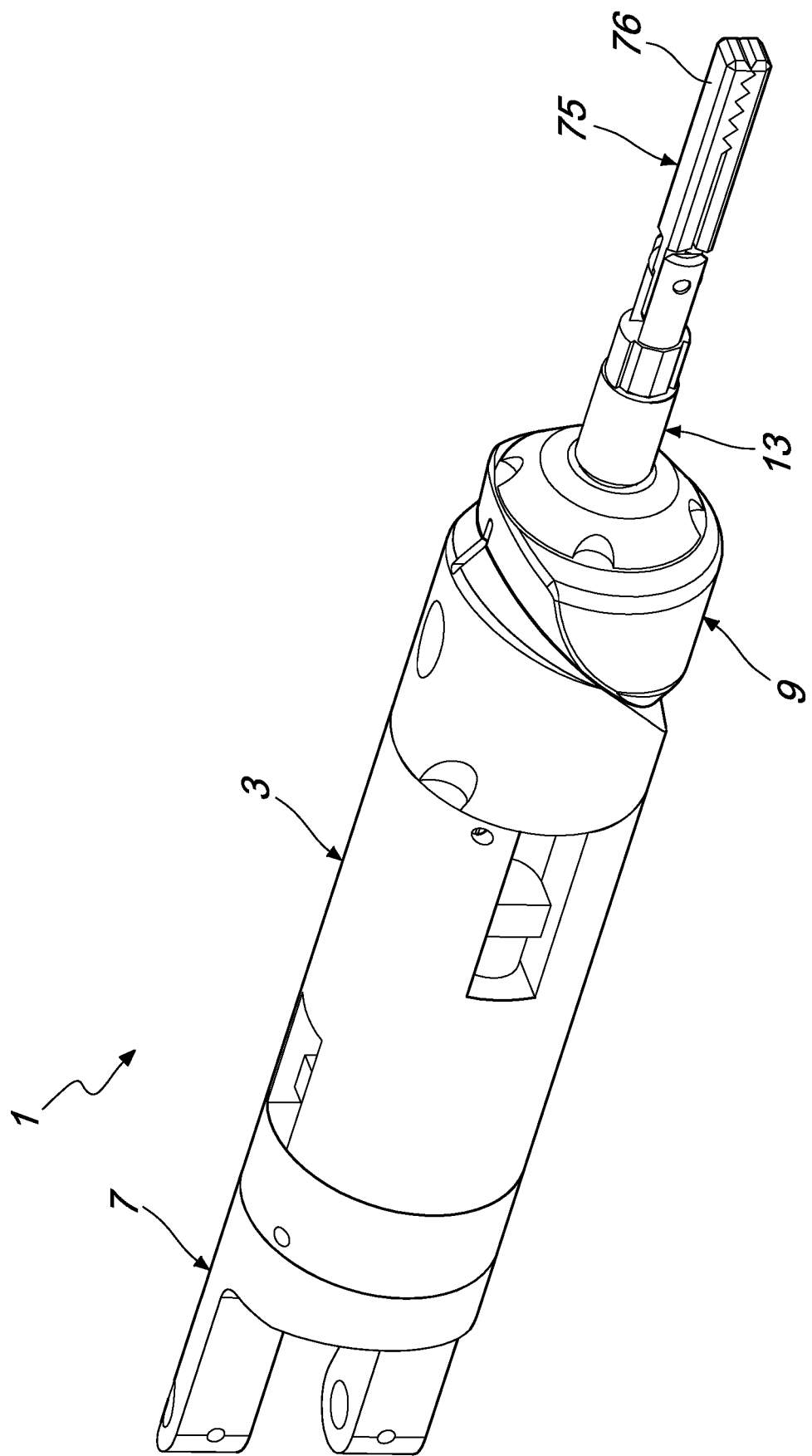
FIG. 1 is a perspective view of an embodiment of an articulated device, according to the disclosure.

With reference to the figures, the articulated device, generally designated by the reference numeral 1, comprises:
- a first rigid body 3, which is configured to rotate about a first rotation axis 5 with respect to a rigid base body 7, a second rigid body 9, which is configured to rotate about a second rotation axis 11 with respect to the first rigid body 3, and a third rigid body 13, which is configured to rotate about a third rotation axis 15 with respect to the second rigid body 9.

Figure 23:
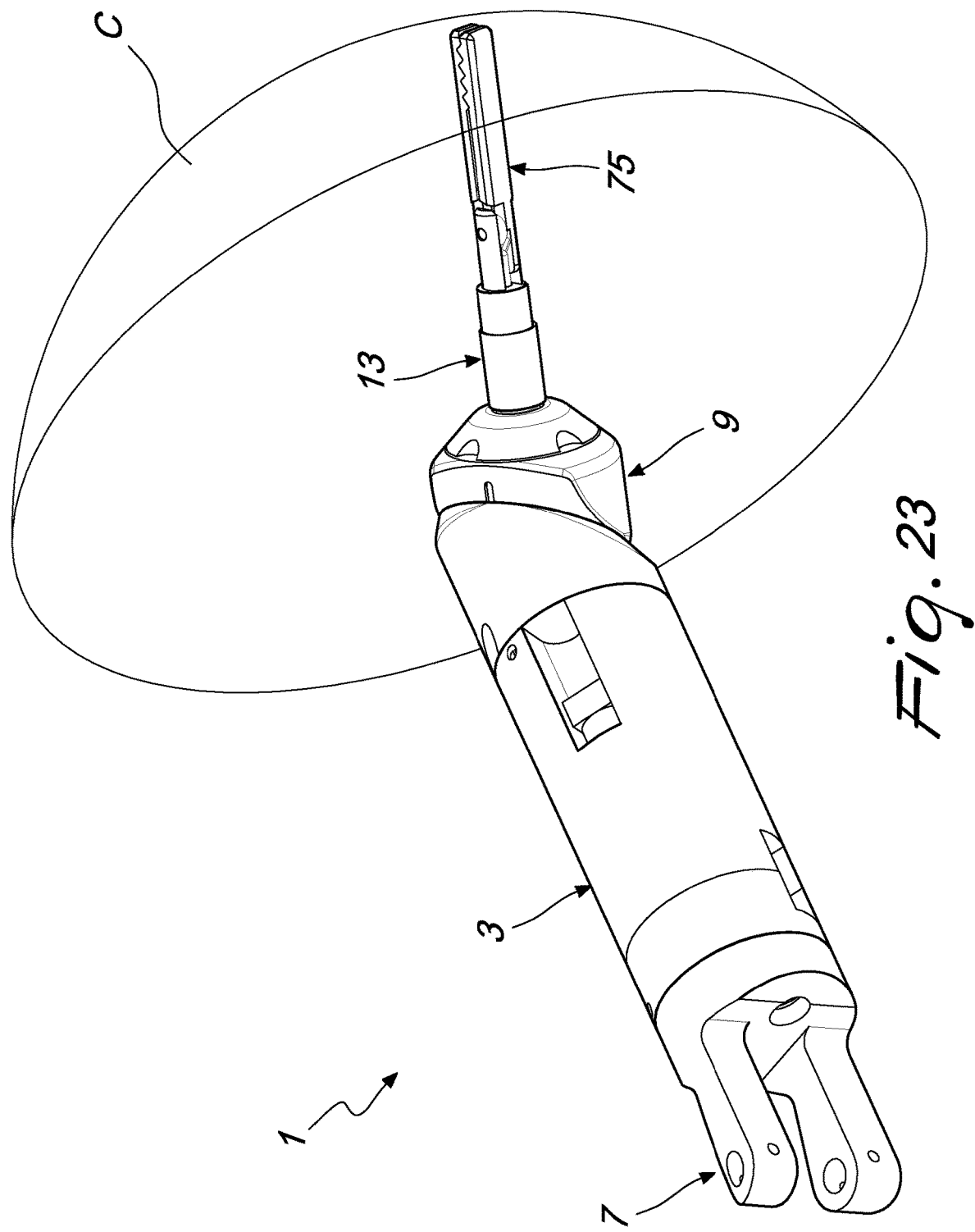
FIG. 23 is a perspective view of the articulated device in FIG. 1, according to the disclosure, illustrating the work space thereof

According to the disclosure, the first rotation axis 5, the second rotation axis 11 and the third rotation axis 15 coincide in at least one point P, which defines the center of rotation of the articulated device 1. In this manner, the articulated device 1 advantageously provides a spherical joint. As shown in FIG. 23, the surface traced by the end point of the terminal element of the articulated device 1, i.e., the work space of the articulated device 1, is a spherical dome C centered in the point P of intersection of the rotation axes.

Advantageously, the second rotation axis 11 is inclined with respect to the first rotation axis 5. Preferably, the second rotation axis 11 is inclined with respect to the first rotation axis 5 by an angle comprised in the interval between 30° and 60° and even more preferably by an angle equal to approximately 45°. In the embodiment of the articulated device 1 shown in the accompanying figures, such angle is approximately equal to 35°.

In some operating configurations, the third rotation axis 15 can coincide with the first rotation axis 5.

The articulated device 1 can also comprise the rigid base body 7, which is configured advantageously to rotate about a fourth rotation axis 17 with respect to an additional rigid reference body, not shown in the accompanying figures.

The articulated device 1 comprises advantageously first rotation means 19 which are adapted to rotate the first rigid body 3 with respect to the rigid base body 7, about the first rotation axis 5.

Such first rotation means 19 comprise advantageously:
a first actuator 21, which is advantageously accommodated in the first rigid body 3 and is rigidly coupled thereto,
a first pinion 23, which is rotationally actuated by the first actuator 21, and
a first ring gear 25, which is rigidly coupled to the rigid base body 7 and is adapted to engage the first pinion 23.

The actuation of the first actuator 21 entails the rotation of the first rigid body 3 with respect to the rigid base body 7 about the first rotation axis 5.

Advantageously, the first rotation means 19 comprise a first four-contact point bearing 27, which is interposed between the rigid base body 7 and the first rigid body 3.

The first four-point contact bearing 27 is advantageously of the ball bearing type. Such bearing comprises a radially external annular element 29, which is integral with the rigid base body 7, and a radially internal annular element 31, which is integral with the first rigid body 3.

Advantageously, the radially internal annular element 31 comprises two annular element halves that can face each other.

Advantageously, the rigid base body 7 and the first rigid body 3 can be mutually fastened in an adjustable manner by way of the fastening and adjustment screws 28.

The integration of the four-point contact bearing in such rotation joint makes it possible to obtain a mechanical structure that is compact, with a smaller axial and radial space occupation and therefore more space available inside the joint, using far fewer parts than alternative constructive solutions; the four-point contact bearing has a high radial and axial load capacity and high rigidity. In order to achieve the same mechanical characteristics, an alternative solution is to use a pair of preloaded roller bearings; however, this last solution requires a higher number of parts and a greater physical space occupation.

Therefore, the integration of the four-point contact bearing in the joint is particularly advantageous for the intra-abdominal surgical robot application.

The articulated device 1 comprises advantageously second rotation means 33 which are adapted to rotate the second rigid body 9 with respect to the first rigid body 3, about the second rotation axis 11.

Such second rotation means 33 advantageously comprise:
a second actuator 35, which is advantageously accommodated in the first rigid body 3 and is rigidly coupled thereto, and
a pair of gears 37, for example of the type of a bevel gear pair, comprising a first gear 41 which is rotated by the second actuator 35, by way of motion transmission means 39, and a second gear 43, which is integral with the second rigid element 9.

The motion transmission means 39 advantageously comprise a second pinion 45, which is rotated by the second actuator 35, and a gear 47 which engages the pinion 45 and, being integral with the first gear 41 of the gear pair 37, transmits its rotation.

The actuation of the second actuator 35 entails the rotation of the second rigid body 9 with respect to the first rigid body 3, about the second rotation axis 11. The angle of inclination defined by the pair of gears 37 determines the angle of inclination of the second rotation axis 11 with respect to the first rotation axis 5.

Advantageously, the second rotation means 33 comprise a second four-point contact bearing 49, which is interposed between the first rigid body 3 and the second rigid body 9.

The second four-point contact bearing 49 is advantageously of the ball bearing type. Such bearing comprises a radially external annular element 51, which is integral with the second rigid body 9, and a radially internal annular element 53, which is integral with the first rigid body 3. Advantageously, the radially internal annular element 53 comprises two annular element halves which can face each other.

The first rigid body 3 and the second rigid body 9 can be advantageously fastened adjustably with respect to each other with the interposition of the second four-point contact bearing 49, by way of a plurality of fastening and adjustment screws 55. Advantageously, there can be three fastening and adjustment screws 55 arranged around the second rotation axis 11.

The integration of the four-point contact ball bearing in such rotation joint makes it possible to obtain a mechanical structure that is compact, with a smaller axial and radial space occupation and therefore more space available inside the joint, using far fewer parts than alternative constructive solutions; the four-point contact ball bearing has a high radial and axial load capacity and high rigidity. To obtain the same mechanical characteristics, an alternative solution is to use a pair of preloaded roller bearings; however, this last solution requires a higher number of parts and a greater physical space occupation.

Therefore, the integration of the four-point contact ball bearing in the joint is particularly advantageous for the intra-abdominal surgical robot application.

The articulated device 1 advantageously comprises third rotation means 57 which are adapted to rotate the third rigid body 13 with respect to the second rigid body 9, about the third rotation axis 15.

Such third rotation means 57 advantageously comprise:
- a third actuator 59, which is accommodated advantageously within the first rigid body 3 and is rigidly coupled thereto,
- a third pinion 61, which is rotated by the third actuator 59, and
- a gear 63, which is adapted to engage the third pinion 61 and is coupled rigidly to a flexible hollow shaft 65.

The flexible hollow shaft 65 is coupled rotationally to the third rigid body 13, so that the rotation imparted by the third actuator 59 is transmitted to the third rigid body 13, which consequently can rotate about the third rotation axis 15.

The flexible hollow shaft 65 is advantageously coupled to the gear 63 by way of a first key-like end 67, which is configured to engage within such gear 63.

On the opposite side, the flexible hollow shaft 65 comprises advantageously a second key-like end 69, which is configured to engage within a corresponding cavity 71 provided in the third rigid body 13. In particular, the second key-like end 69 can have a square or rectangular transverse cross-section, and correspondingly a square or rectangular cavity 71 can be provided in the third rigid body 13.

The flexible hollow shaft 65 is advantageously made of a flexible material, since it must be able to bend when the second rigid body 9 rotates with respect to the first rigid body 3 about the second rotation axis 11.

Therefore, the flexible hollow shaft 65 is adapted to transmit the rotation about the third rotation axis 15 to the third rigid body 13 regardless of the operating configuration assumed by the second rigid body 9.

In particular, the second key-like end 69 is configured to be able to freely slide axially within the cavity 71 of the third rigid body 13, so that, regardless of the operating configuration assumed by the second rigid body 9, the flexible hollow shaft 65 is in any case capable of transmitting the rotation to the third rigid body 13.

Figure 2:
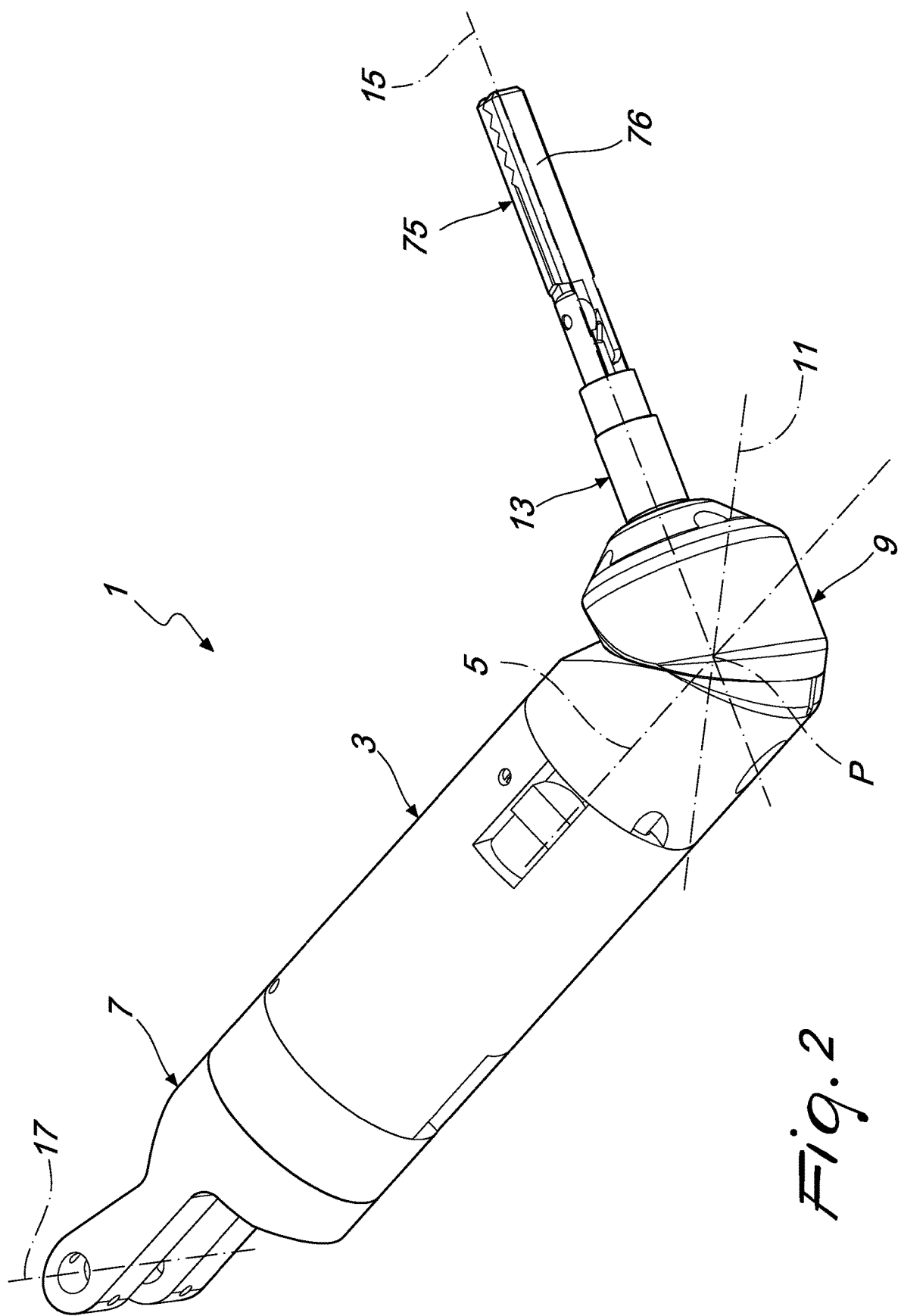
FIG. 2 is another perspective view of the articulated device in FIG. 1, according to the disclosure, showing the rotation axes of the rigid bodies that make up the articulated device.
Figure 3:
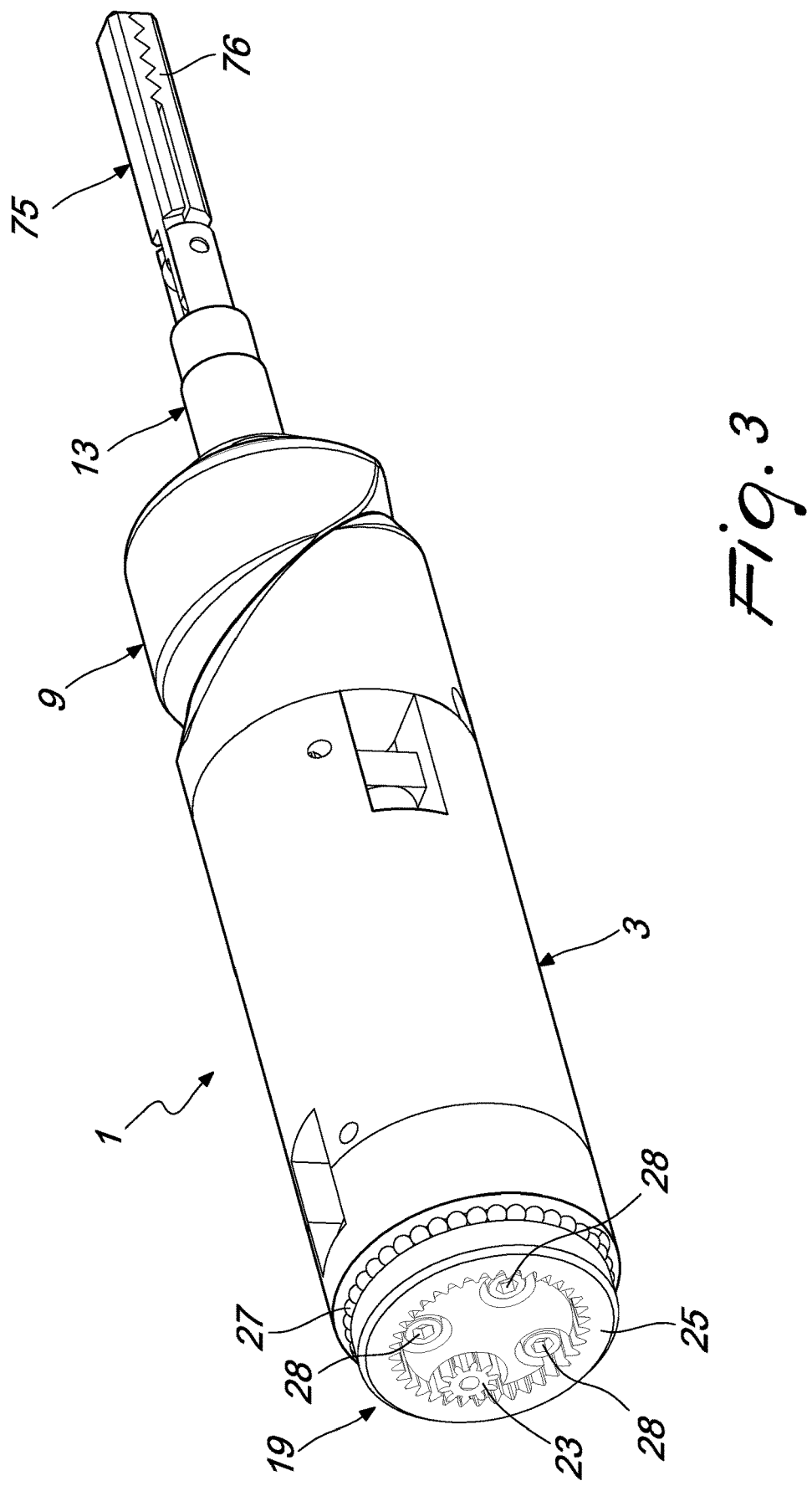
FIG. 3 is another perspective view of the articulated device in FIG. 1, according to the disclosure, in which the rigid base body has been removed.
Figure 4:
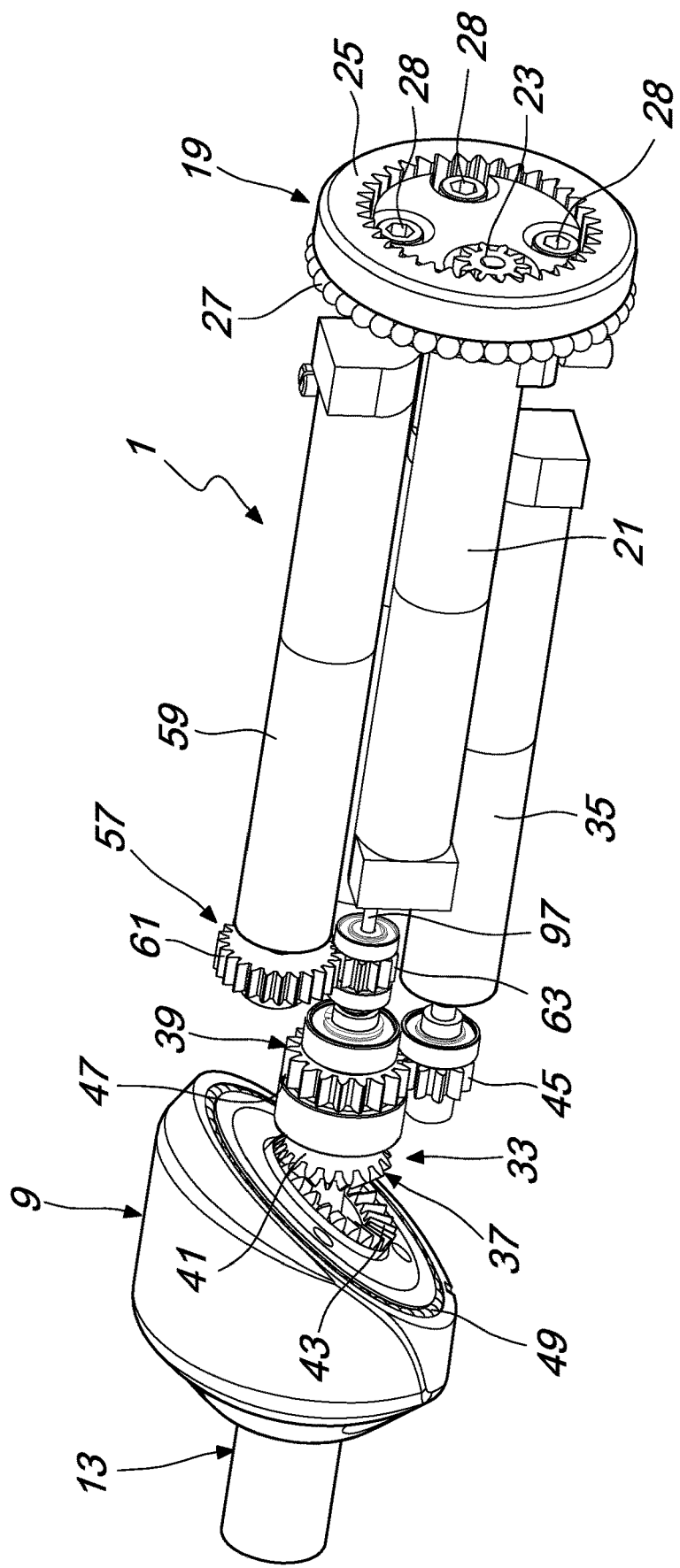
FIGS. 4 and 5 are two different perspective views of some internal components of the articulated device in FIG. 1, according to the disclosure.
Figure 5:
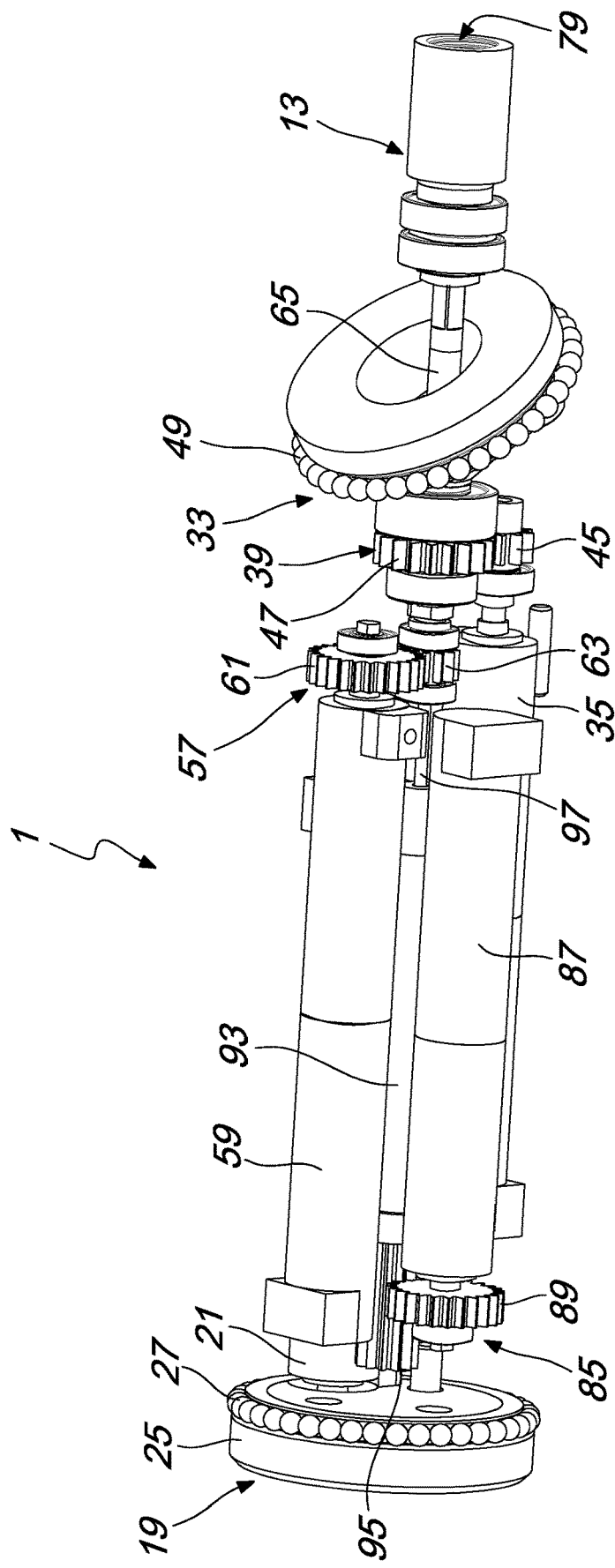
Figure 8:
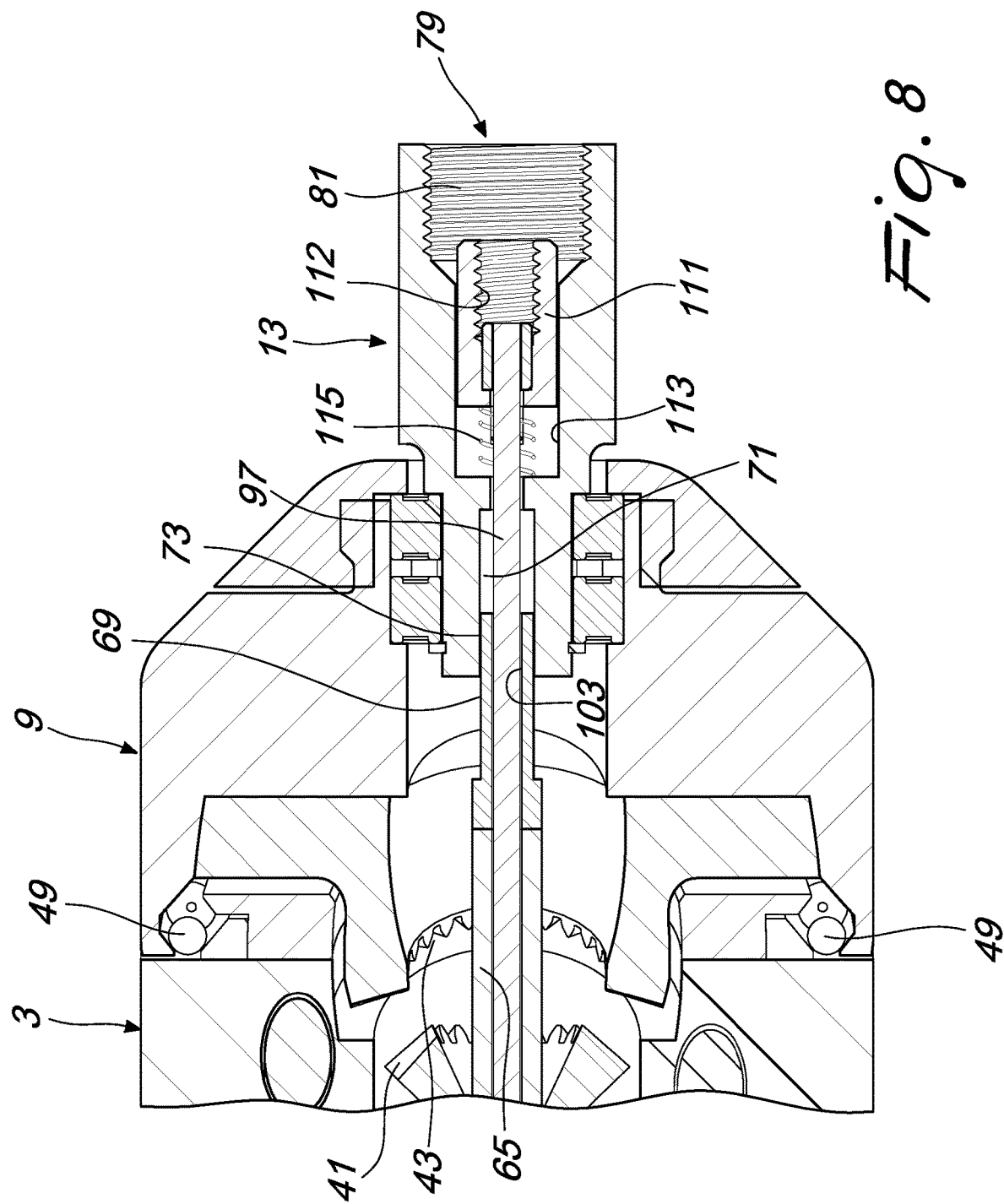
FIG. 8 is an enlarged-scale view of a portion of FIG. 6, in which however the terminal operating instrument has been removed.
Figure 9:
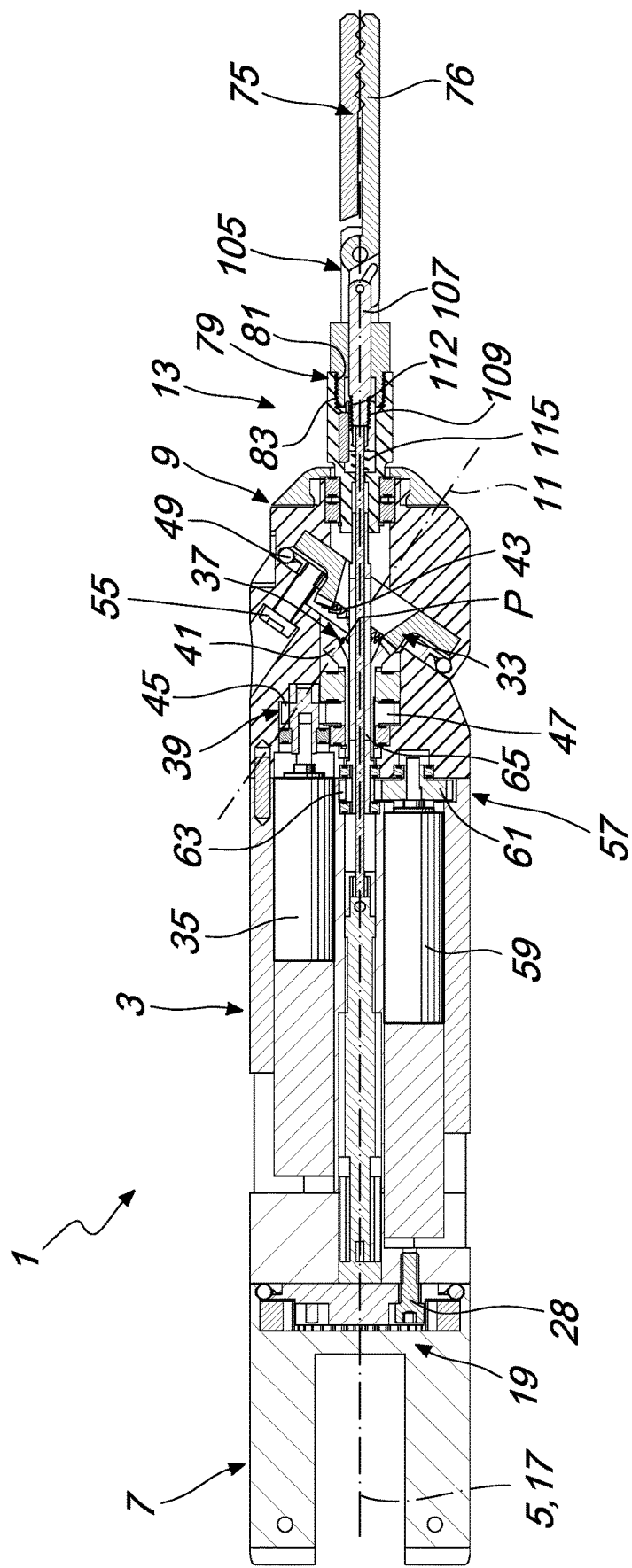
FIG. 9 is a cross-sectional side view of the articulated device in FIG. 1, according to the disclosure.
Figure 10:
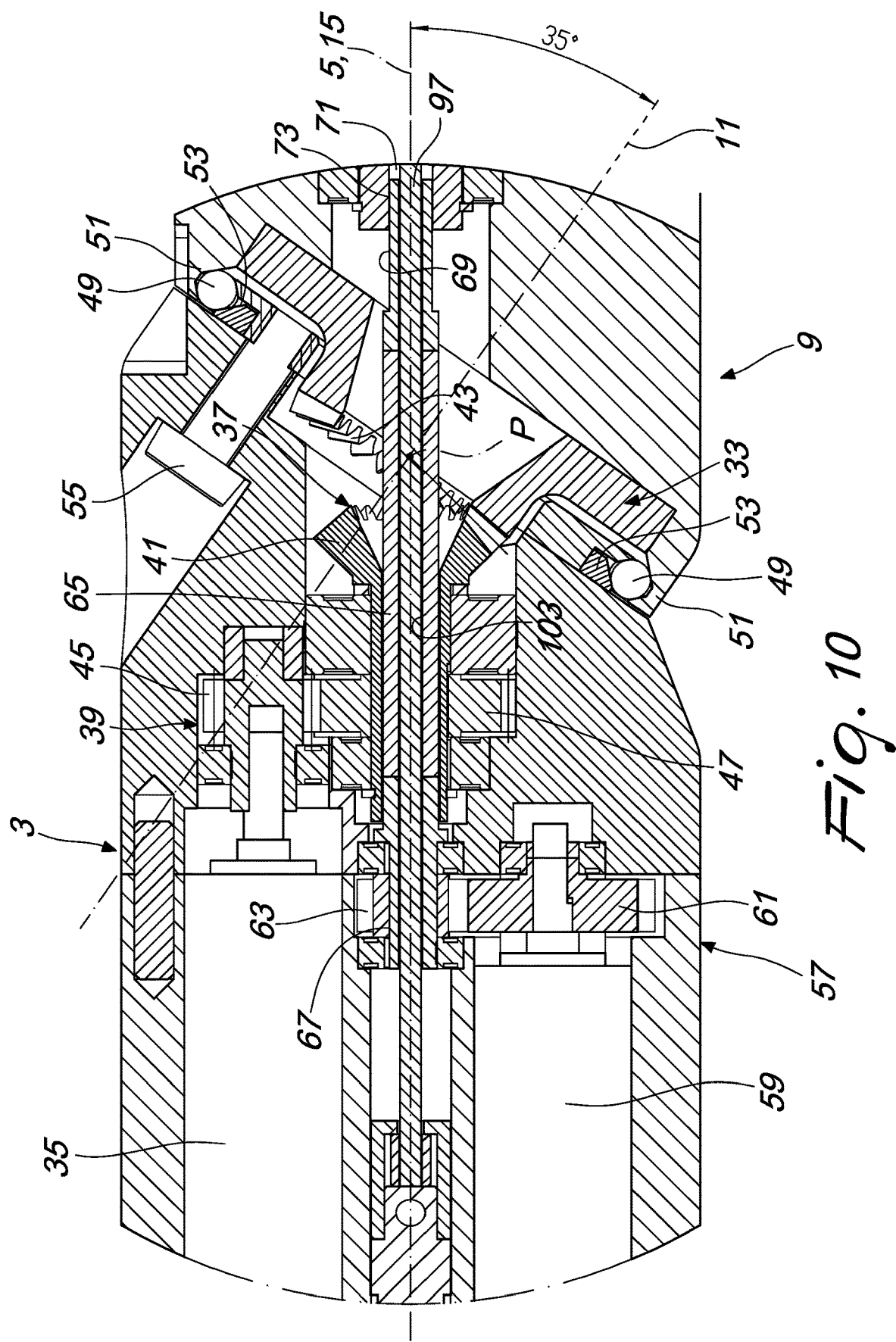
FIGS. 10 and 11 are enlarged-scale views of two different portions of FIG. 9.
Figure 11:
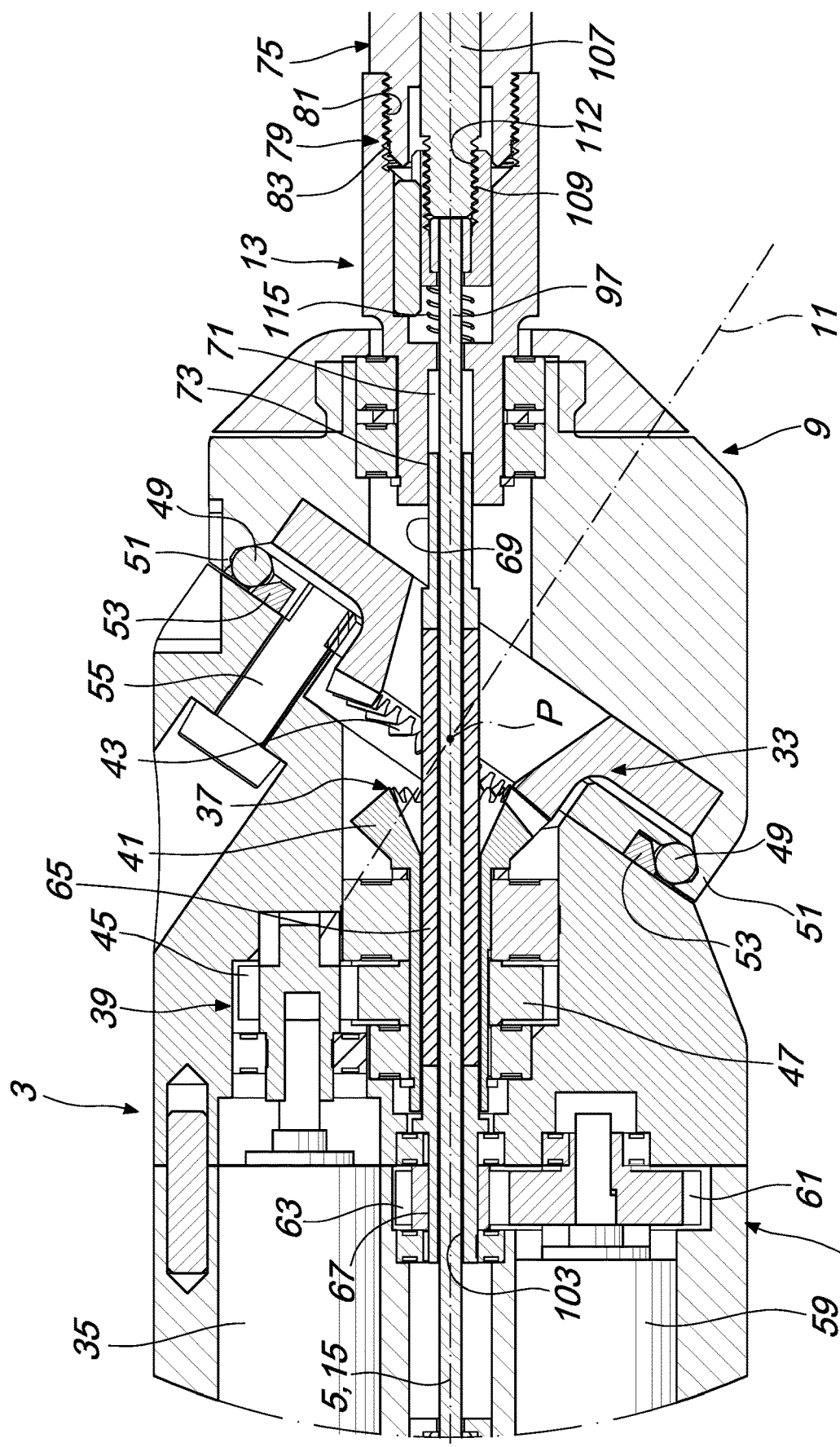
Figure 12:
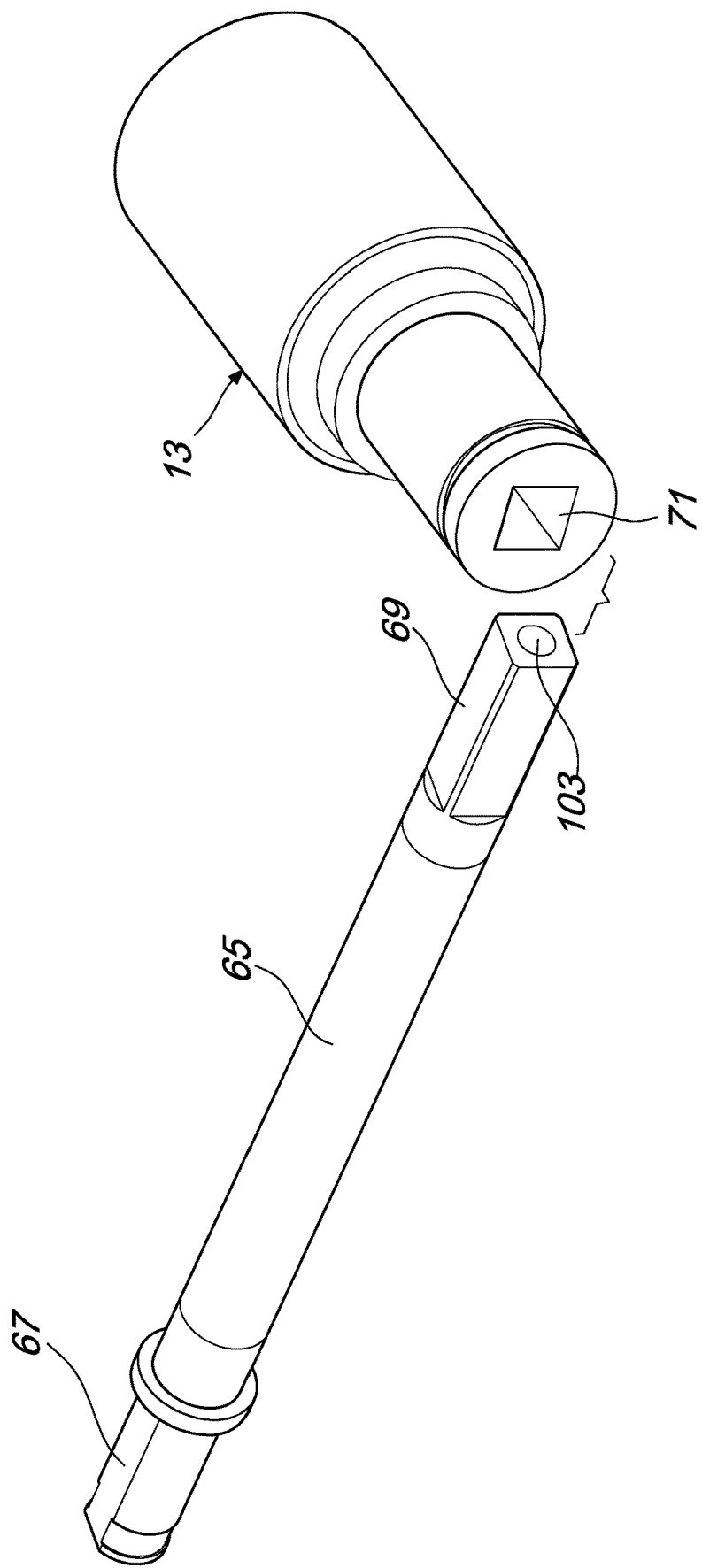
FIG. 12 is a view of two mechanical motion transmission components of the articulated device, according to the disclosure.
Figure 13:
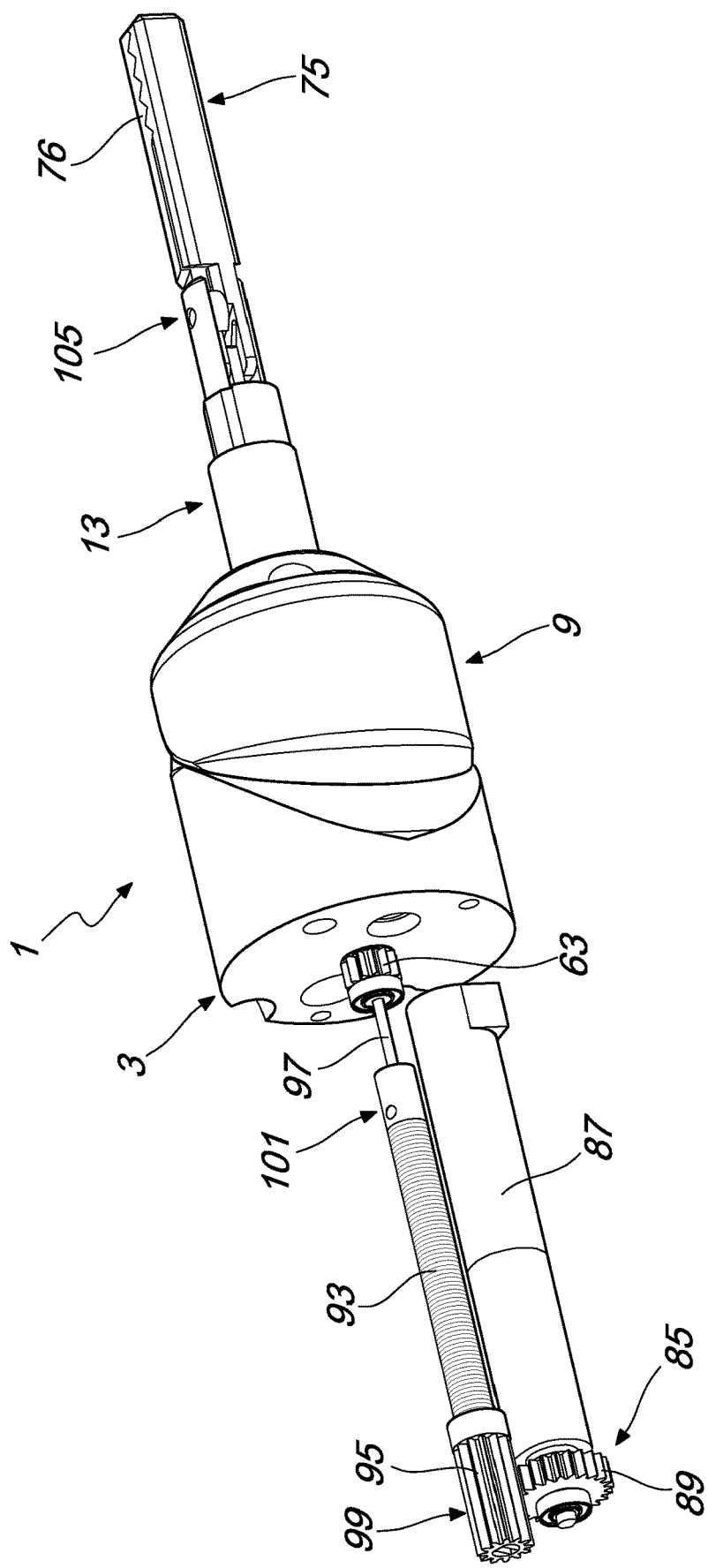
FIG. 13 is another perspective view of the articulated device in FIG. 1, according to the disclosure, showing only some mechanical components.
Figure 14:
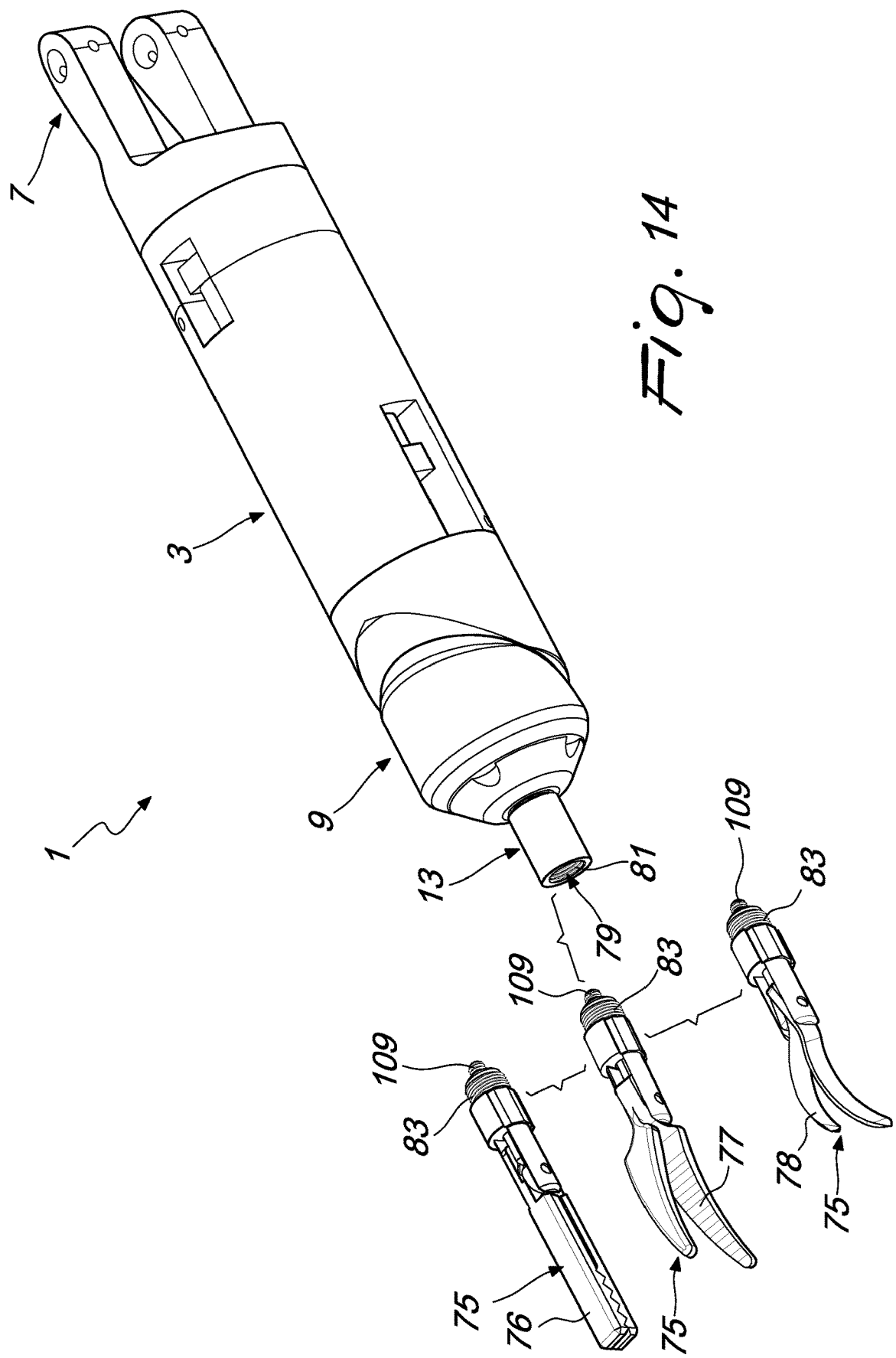
FIG. 14 is another perspective view of the articulated device in FIG. 1, according to the disclosure, showing the possibility of coupling with different terminal operating instruments.
Figure 15:
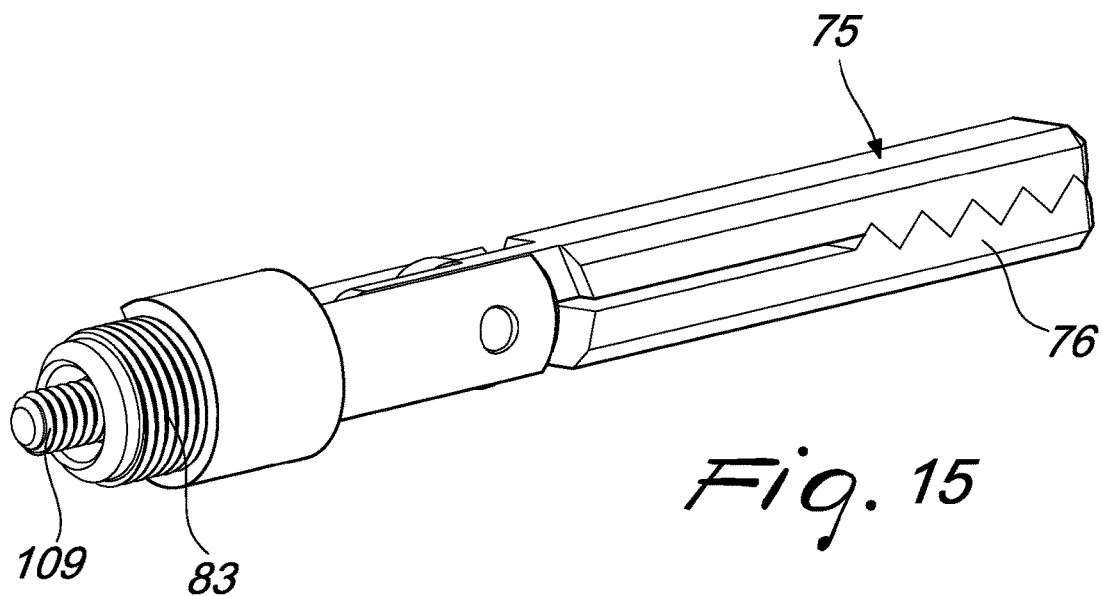
FIG. 15 is a perspective view of one type of terminal operating instrument that can be associated with the articulated device in FIG. 1, according to the disclosure.
Figure 16:
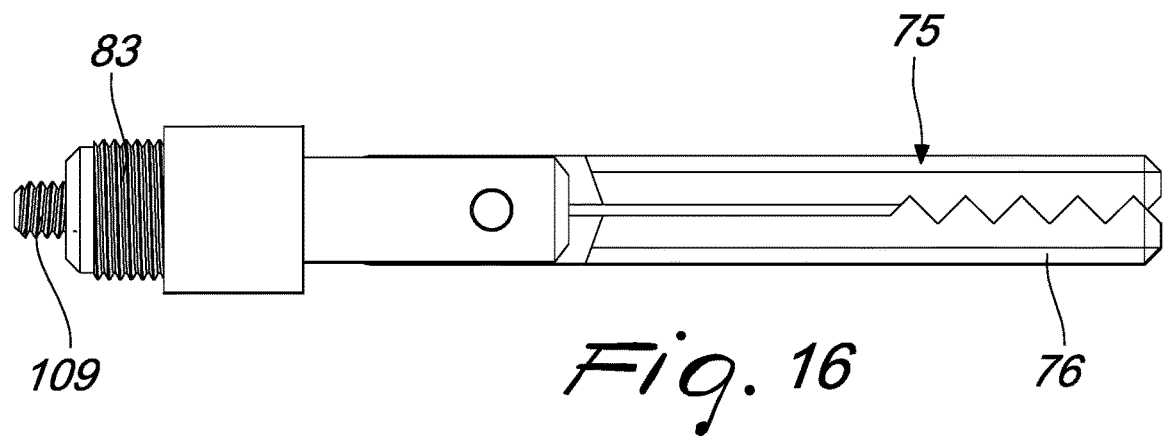
FIG. 16 is a side view of the operating instrument in FIG. 15.
Figure 17:
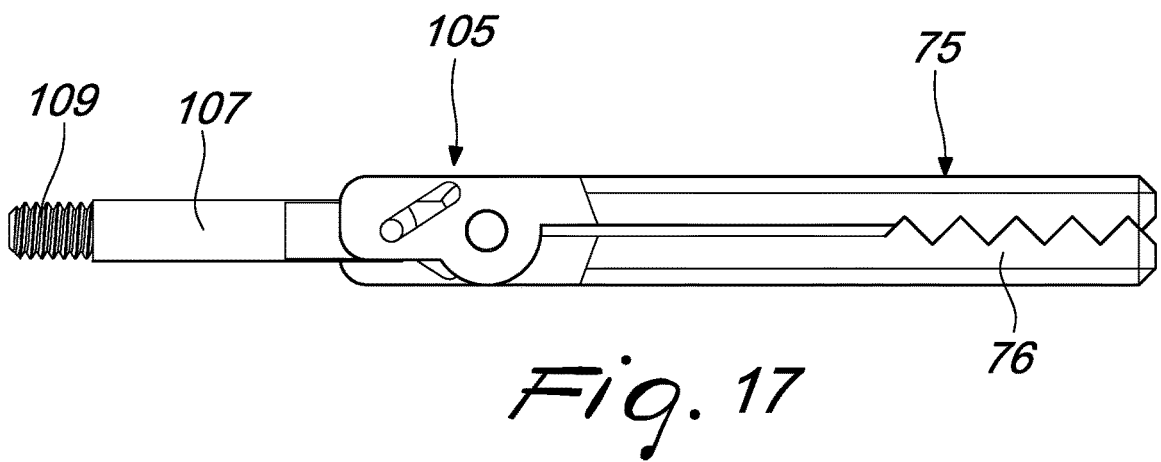
FIG. 17 is a side view of the internal component of the operating instrument in FIG. 15.
Figure 18:
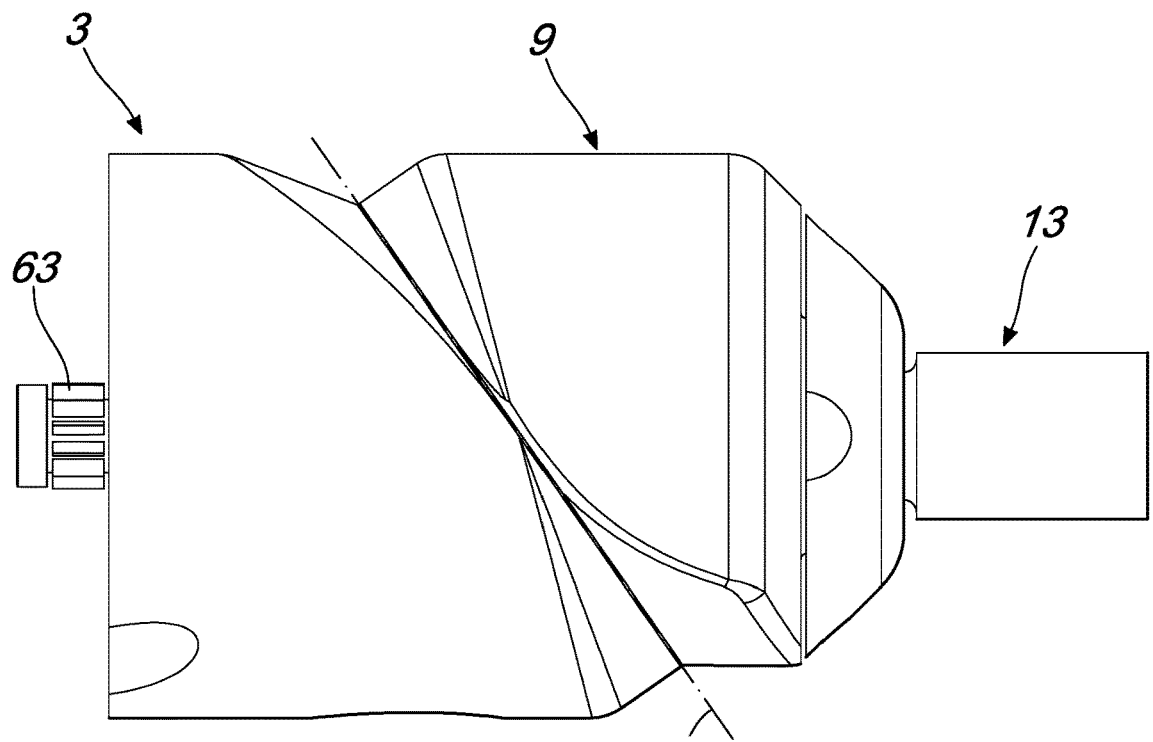
FIGS. 18 to 22 relate to an alternative embodiment of the means of rotation between two rigid bodies of the articulated device, according to the disclosure.

In particular, as can be seen for example from FIG. 11, when the first rotation axis 5 and the third rotation axis 15 are aligned, the second key-like end 69 engages in the cavity 71 only along the portion 73. If the second rigid body 9 assumes a different operating configuration, for example such as the one shown in FIG. 2, then the second key-like end 69 can slide further within the cavity 71, keeping the rotational coupling active in both cases.

The articulated device 1 can be adopted for any type of articulation of a robotic system.

Advantageously, the articulated device 1, according to the embodiment shown in the accompanying figures, is adopted for a terminal articulation of a robotic system, i.e., an articulation that supports, moves, and optionally actuates a terminal operating instrument 75, such as graspers 76, a dissector is 77, or scissors 78.

Advantageously, therefore, the articulated device 1 can comprise means 79 of fixing an operating instrument 75 to the third rigid body 13. Advantageously, the fixing means 79 comprise a threaded cavity 81 which is configured to engage a corresponding threaded portion 83 of the operating instrument 75.

Advantageously, furthermore, the articulated device 1 comprises means 85 of actuating the operating instrument 75. In particular, the actuation means 85 are adapted to allow the opening and closing of the graspers 75 or of the scissors 77.

Such actuation means 85 advantageously comprise:
- a fourth actuator 87, which is advantageously accommodated within the first rigid body 3 and is rigidly coupled thereto,
- a fourth pinion 89, which is rotated by the fourth actuator 87,
- a worm gear 93, which has, at a first end 99, a gear 95, which is integral therewith; such gear 95 is configured to engage the fourth pinion 89 and therefore to rotate the worm gear 93,
- a threaded through hole 91, provided in the first rigid body 3 along the axis of longitudinal extension of such first rigid body 3, configured to be passed through by the worm gear 93; the rotation of the worm gear 93 within the threaded through hole 91 determines an axial movement of such worm gear 93, and
- a flexible cable 97, which is associated, at a first end, with the second end 101 of the worm gear 93, and can be associated, at the second end, with the operating instrument 75, as explained below; in order to reach the operating instrument 75, the flexible cable passes through the through hole 103 of the flexible hollow shaft 65.

Furthermore, the operating instrument 75 comprises advantageously a lever system 105, the traction and/or thrust of which entails the opening and/or closure of the graspers 76 or of the scissors 77. The traction and/or thrust of such lever system 105 is obtained by way of a rod 107 which has a threaded end 109.

The third rigid body 13, in addition to comprising the fixing means 79 with the threaded cavity 81, also comprises a block 111, with a threaded cavity 112, which can slide within a cavity 113 provided in the rigid third rigid body 13, and is coupled to the second end of the flexible cable 97.

Essentially, the actuation of the operating instrument 75, in order to open and close the graspers 76, is as follows.

The actuator 87 rotates the fourth pinion 89, which transmits the motion to the gear 95, which rotates about its own axis integrally with the worm gear 93. Consequently, the worm gear 93 screws into the threaded through hole 91 provided in the first rigid element 3, thus advancing or retracting along the axis of longitudinal extension of such first rigid body 3.

The advancement of the worm gear 93, which also entrains with it the gear 95, is allowed by the fact that the gear 95 has a longitudinal extension that is such as to always be meshed with the fourth pinion 89, in any operating configuration.

The axial movement of the worm gear 93 causes the thrust or the traction of the flexible cable 97, which produces the axial motion of the block 111 within the cavity 113 and consequently of the rod 107 connected thereto by way of the threaded end 109. The thrust or the traction of the threaded rod 107 actuates the lever system 105, which opens and closes the graspers 76 or the scissors 77.

Advantageously, in order to allow the correct fixing, by screwing, of the operating instrument 75 to the third rigid body 13, the threading of the threaded cavity 81 and the threading of the threaded cavity 112 of the block 111 have the same pitch.

Furthermore, in order to allow correct screwing, the block 111 can have a "key-like" external shape, configured to remain integral in rotation with the third rigid body 13. In particular, on the outer lateral surface of the block 111 there can be an axial hollow, configured to engage a corresponding axial lip that protrudes from the internal lateral surface of the third rigid body 13. The lip can slide axially within the hollow but is coupled rotationally thereto.

Furthermore, advantageously there is a spring 115 which, in the inactive configuration, keeps the sliding block 111 pushed outward, so that, upon the screwing of the operating instrument 75, the threaded end 109 of the rod 107 is screwed correctly within the block 111.

By virtue of the mechanism described above, the tool changing operation occurs by way of a single movement: by keeping the terminal operating instrument rotationally locked and turning the output shaft (rigid body 13) one achieves simultaneously the disengagement (or engagement) of the external body of the operating instrument and of the corresponding internal actuation rod 107. This characteristic makes the mechanism particularly adapted for the tool changing of terminal operating instruments during the surgical procedure. Advantageously, the articulated device 1 comprises an alternative embodiment of the second rotation means which are adapted to rotate the second rigid body 9 with respect to the first rigid body 3, about the second rotation axis 11, designated by the reference numeral 133.

According to such alternative embodiment, the second rotation means 133 comprise advantageously:

- a second actuator 135, which is advantageously accommodated within the first rigid body 3 and is rigidly coupled thereto, and
- a second flexible hollow shaft 137, which comprises a first end 141 which is rotated by the second actuator 135 by way of motion transmission means 139, and a second end 143, which rotates integrally with the second rigid body 9.

The motion transmission means 139 advantageously comprise a second pinion 145, which is rotated by the second actuator 135, and a ring gear 147, which engages the pinion 145 and, being integral with the first end 141 of the second flexible hollow shaft 137, transmits its rotation.

Advantageously, the second end 143 comprises a key-like element 151, which is configured to be accommodated in a corresponding key-like seat 153 provided in the second rigid body 9. The key-like element 151 inserted in the key-like seat 153 makes it possible to transmit the rotation of the second flexible hollow shaft 137 to the second rigid body 9.

The second flexible hollow shaft 137 is advantageously made of a flexible material, since it must be able to bend when the second rigid body 9 rotates with respect to the first rigid body 3 about the second rotation axis 11.

The second rigid body 9 faces the first rigid body 3 along a plane 150 which is inclined with respect to the first rotation axis 5. In its rotation, the second rigid body 9 is coupled so as to maintain contact with the first rigid body 3 along such inclined plane 150, and this determines the rotation of the second rigid body 9 about the second rotation axis 11, at right angles to such plane 150. The angle of inclination defined by such plane 150 determines the angle of inclination of the second rotation axis 11 with respect to the first rotation axis 5.

Figure 19:
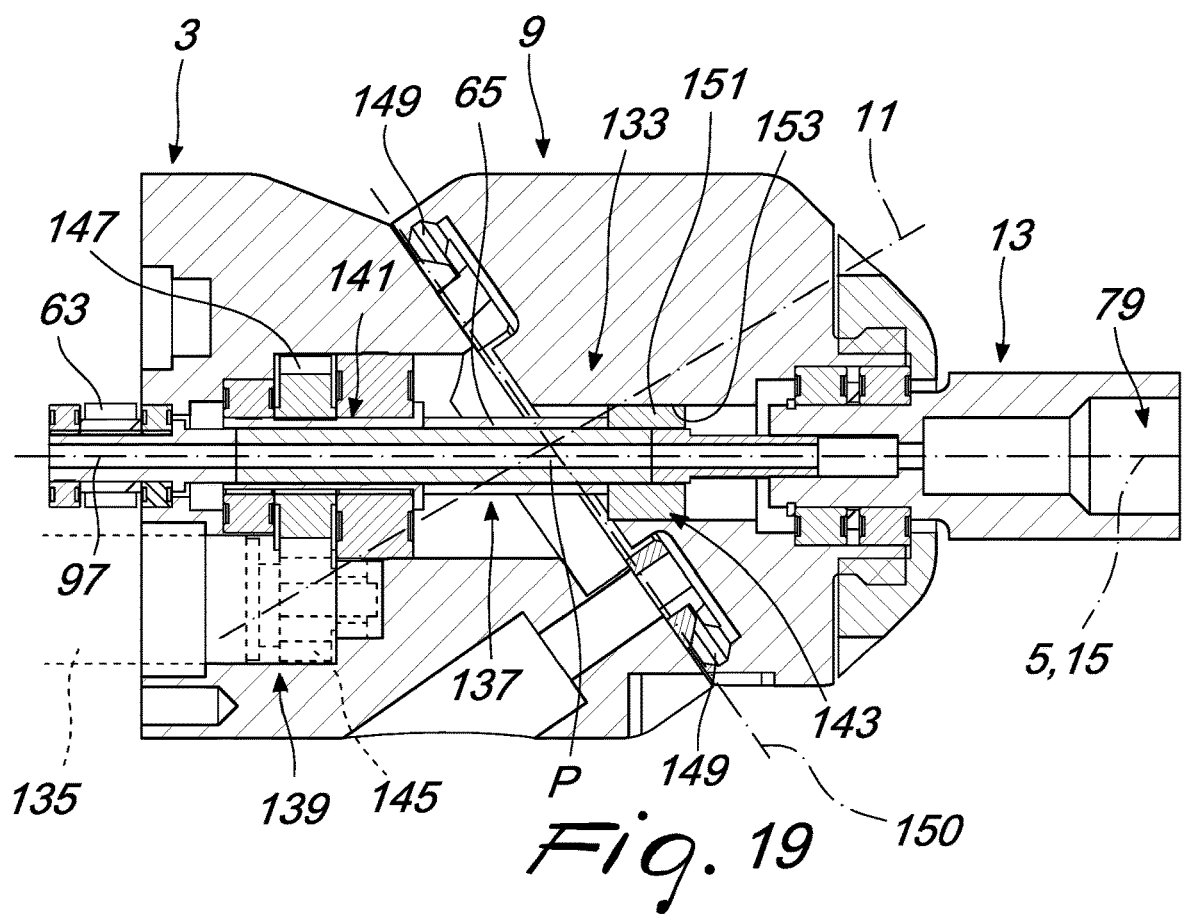
Figure 20:
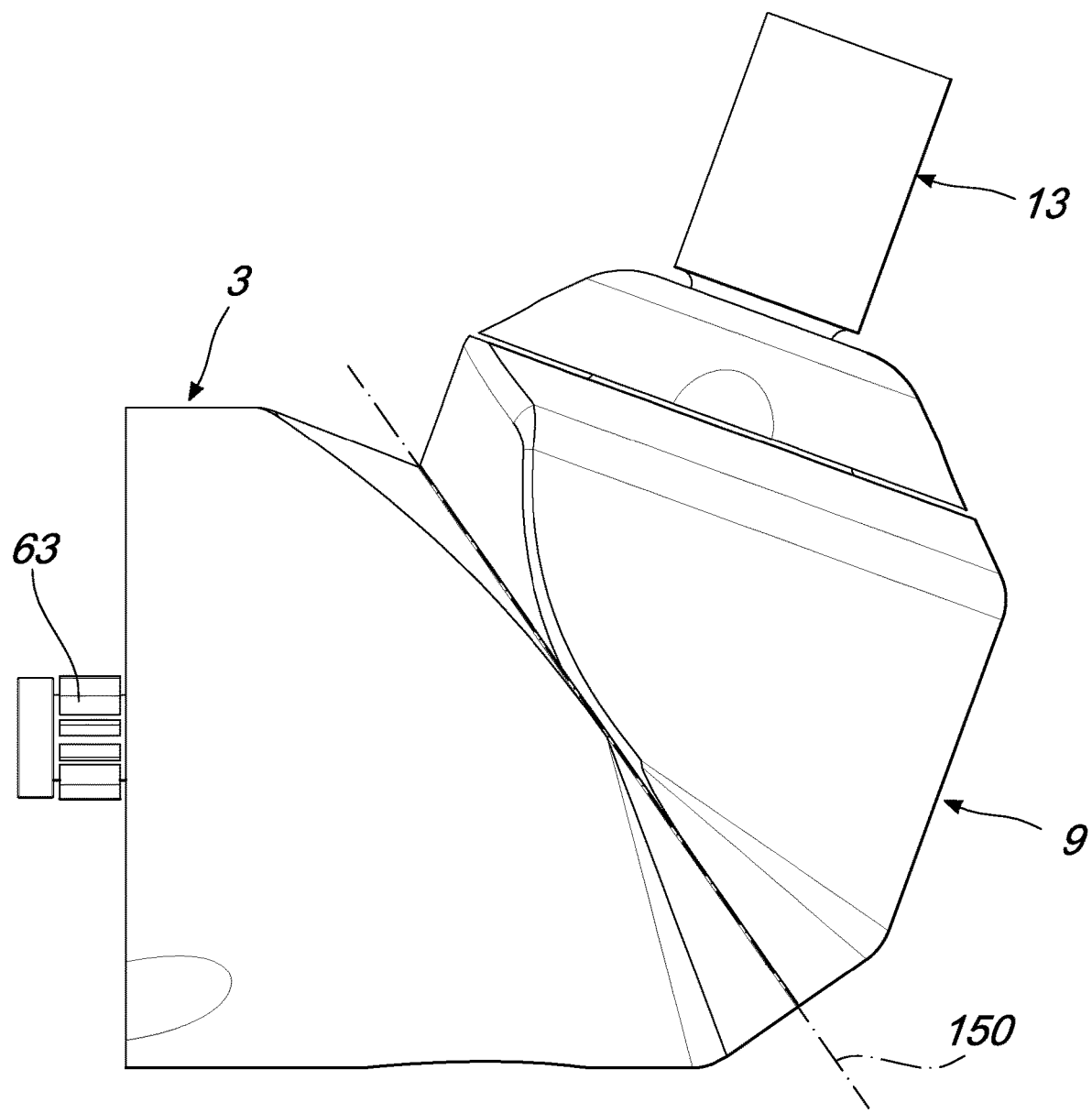
Figure 21:
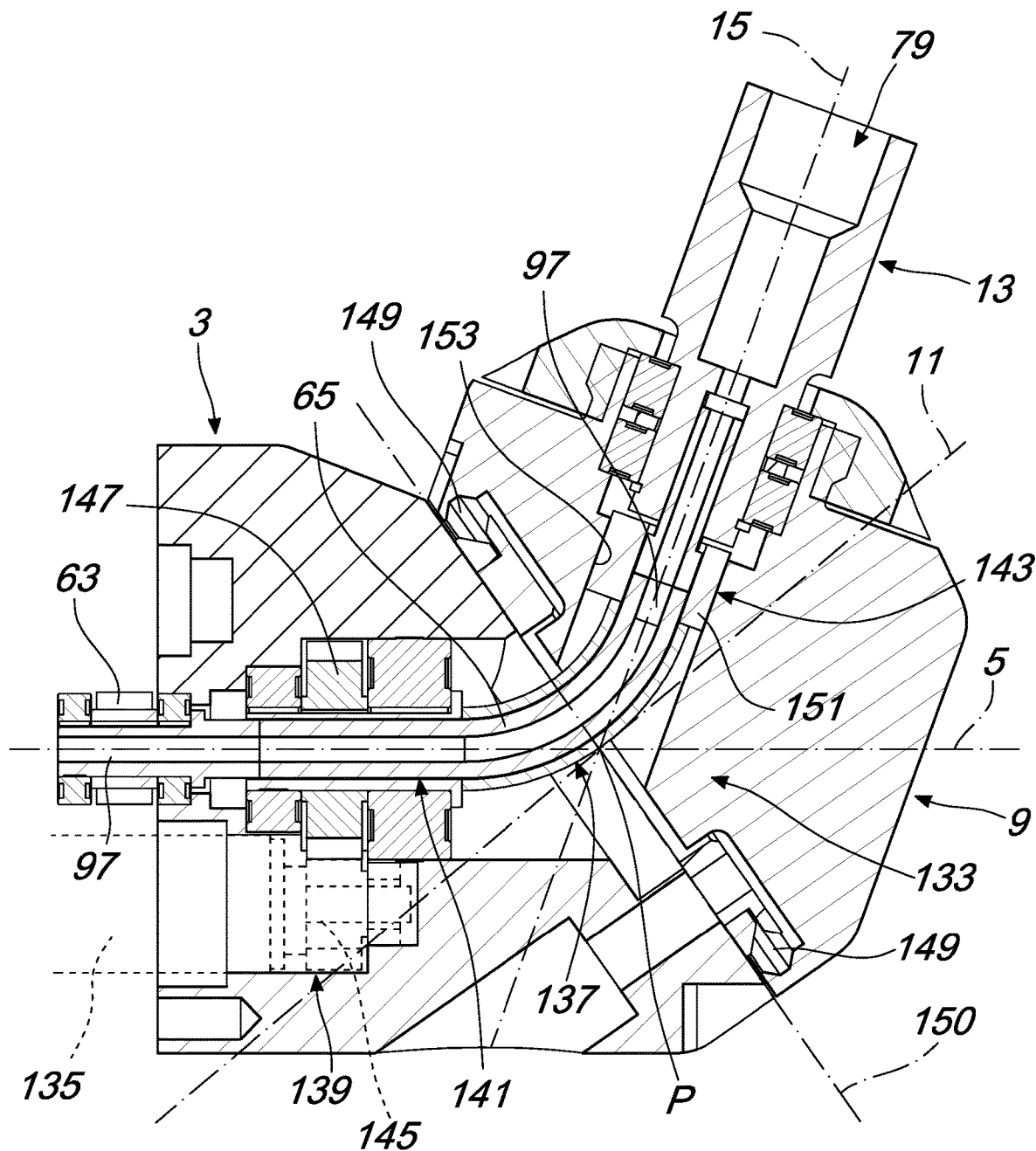
Figure 22:
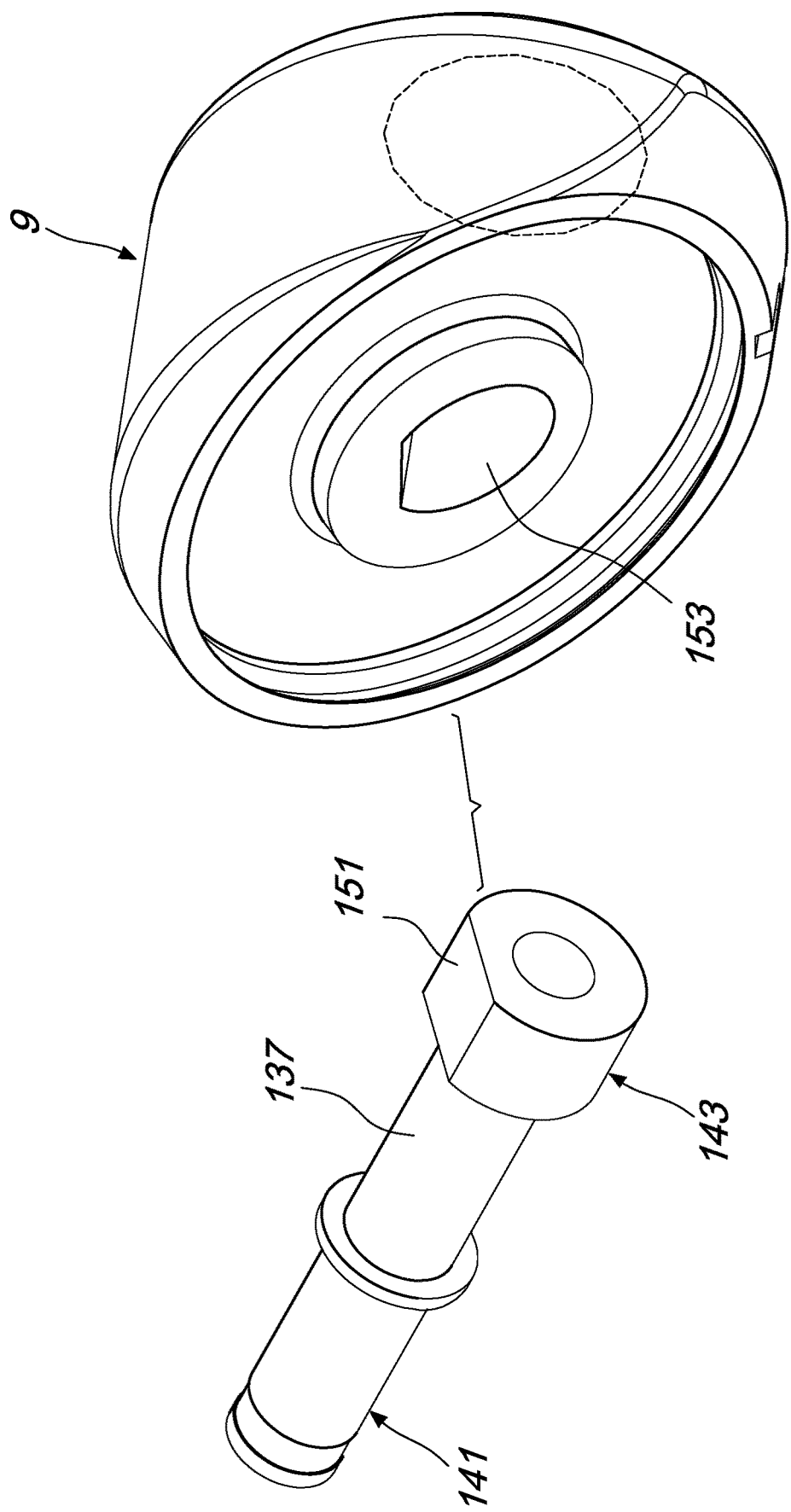

Advantageously, so that the second flexible hollow shaft 137 can transmit the rotation to the second rigid body 9 in any operating configuration assumed by such second rigid body 9, the key-like element 151 is free to slide axially within the key-like seat 153. In particular, by comparing the operating configuration of the second rigid body 9 shown in FIG. 19 with the operating configuration shown in FIG. 21, it can be seen that the distance between the second end 143 of the second flexible hollow shaft 137 and the third rigid body 13 varies depending on the operating configuration assumed by such second rigid body 9.

The second flexible hollow shaft 137 is advantageously configured to contain, coaxially, the flexible hollow shaft 65 that belongs to the third rotation means 57 as described above. And likewise, the flexible hollow shaft 65 can coaxially accommodate the flexible cable 97, which belongs to the actuation means 85.

Advantageously, the second rotation means 133 comprise a second four-point contact bearing 149, which is interposed between the first rigid body 3 and the second rigid body 9. Such second four-point contact bearing 149 is configured to ensure the sliding between the respective facing surfaces of the first rigid body 3 and of the second rigid body 9.

The operation of the articulated device is clear and evident from the foregoing description.

The particular configuration of the rotation means 19, 33 and 57 makes it possible to actuate the articulated device 1 within a spherical dome C which has as its center of origin a point P that coincides with the center of rotation of such articulated device 1.

Furthermore, the presence of additional actuation means 85 also makes it possible to actuate a terminal operating instrument 75, which can conveniently be connected to the articulated device 1.

In practice it has been found that the articulated device, according to the present disclosure, achieves the intended aims and objectives, since it makes it possible to achieve very high levels of dexterity.

Another advantage of the articulated device, according to the disclosure, is that it can assume miniaturized dimensions.

A further advantage of the articulated device, according to the disclosure, is that it can be adopted in robotic systems that are adapted to operate in the field of minimally-invasive robotic surgery, where work spaces are very confined and limited, and where extreme accuracy is required.

Another advantage of the articulated device, according to the disclosure, is that it can be adopted for any articulation of a robotic system, although it is particularly adapted for terminal articulations that operate an operating instrument.

The articulated device thus conceived is susceptible of numerous modifications and variations, all of which are within the scope of the inventive concept.

All the details may furthermore be replaced with other, technically equivalent elements.

In practice, the materials used, as long as they are compatible with the specific use, as well as the contingent shapes and dimensions, may be any according to the requirements.

The invention claimed is:

1. An articulated device for robotic systems, comprising:
   a first rigid body configured to rotate about a first rotation axis with respect to a rigid base body,
   a second rigid body configured to rotate about a second rotation axis with respect to said first rigid body, and
   a third rigid body configured to rotate about a third rotation axis with respect to said second rigid body,
   wherein said first rotation axis, said second rotation axis, and said third rotation axis coincide in at least one point, which defines the center of rotation of said articulated device, and further comprising:
   first means for the rotation of said first rigid body with respect to said first rotation axis,
   second means for the rotation of said second rigid body with respect to said second rotation axis, and
   third means for the rotation of said third rigid body with respect to said third rotation axis.

2. The articulated device according to claim 1, wherein said second rotation axis is inclined with respect to said first rotation axis.

3. The articulated device according to claim 1, wherein said second rotation axis is inclined with respect to said first rotation axis by an angle comprised in the interval between 30° and 40°.

4. The articulated device according to claim 1, wherein said first rotation means comprise:
- a first actuator, which is coupled rigidly to said first rigid body,
- a first pinion, which is rotated by said first actuator, and
- a first ring gear, which is coupled rigidly to said rigid base body and is adapted to engage said first pinion,
- the actuation of said first actuator being adapted to rotate said first rigid body with respect to said rigid base body, about said first rotation axis.

5. The articulated device according to claim 4, wherein said second rotation means comprise:
- a second actuator coupled rigidly to said first rigid body, and
- a gear pair comprising a first gear rotated by said second actuator, by way of motion transmission means, and a second gear integral with said second rigid body,
- the actuation of said second actuator being adapted to rotate said second rigid body with respect to said first rigid body, about said second rotation axis.

6. The articulated device according to claim 4, wherein said second rotation means comprise:
- a second actuator rigidly coupled to said first rigid body, and
- a flexible hollow shaft, comprising a first end rotated by said second actuator by way of motion transmission means, and a second end, which rotates integrally with said second rigid body,
- the actuation of said second actuator being adapted to rotate said second rigid body with respect to said first rigid body, about said second rotation axis.

7. The articulated device according to claim 6, wherein said third rotation means comprise:
- a third actuator coupled rigidly to said first rigid body,
- a third pinion rotated by said third actuator, and
- a gear adapted to engage said third pinion and is coupled rigidly to a further flexible hollow shaft,
- said further flexible hollow shaft being coupled rotationally to said third rigid body, so that the rotation imparted by said third actuator is transmitted to said third rigid body in order to rotate said third rigid body about said third rotation axis.

8. The articulated device according to claim 7, wherein said first actuator, said second actuator, and said third actuator are accommodated in said first rigid body.

9. The articulated device according to claim 1, wherein said third rigid body is configured to be associated with a terminal operating instrument, said articulated device comprising means for the actuation of said terminal operating instrument.

10. The articulated device according to claim 9, wherein said actuation means comprise a fourth actuator which is accommodated in said first rigid body.

11. A robotic system comprising an articulated device according to claim 1.

* * * * *